US009335296B2

(12) United States Patent
Le et al.

(10) Patent No.: US 9,335,296 B2
(45) Date of Patent: May 10, 2016

(54) SYSTEMS AND METHODS FOR STEAM GENERATOR TUBE ANALYSIS FOR DETECTION OF TUBE DEGRADATION

(71) Applicant: WESTINGHOUSE ELECTRIC COMPANY LLC, Cranberry Township, PA (US)

(72) Inventors: Qui V. Le, Pittsburgh, PA (US); William K. Cullen, Pittsburgh, PA (US); Craig Bowser, North Huntingdon, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 402 days.

(21) Appl. No.: 13/951,984

(22) Filed: Jul. 26, 2013

(65) Prior Publication Data

US 2014/0097834 A1 Apr. 10, 2014

Related U.S. Application Data

(60) Provisional application No. 61/711,875, filed on Oct. 10, 2012, provisional application No. 61/755,610, filed on Jan. 23, 2013, provisional application No. 61/755,601, filed on Jan. 23, 2013.

(51) Int. Cl.
*G01N 27/72* (2006.01)
*G01N 27/90* (2006.01)

(52) U.S. Cl.
CPC ........ *G01N 27/9046* (2013.01); *G01N 27/9073* (2013.01)

(58) Field of Classification Search
CPC .................... G01N 27/9046; G01N 27/9073
USPC .................................................. 324/228–243
See application file for complete search history.

(56) References Cited

U.S. PATENT DOCUMENTS 4,194,149 A * 3/1980 Holt et al. ...................... 324/220
4,199,975 A * 4/1980 Schrock et al. ................ 73/40.7
(Continued)

FOREIGN PATENT DOCUMENTS

JP 2002090345 A 3/2002
KR 20120059140 A 6/2012

OTHER PUBLICATIONS

International Search Report and Written Opinion of the International Searching Authority for PCT/US2013/063840 dated Aug. 7, 2014 (Forms PCT/ISA/220, PCT/ISA/210, PCT/ISA/237).
(Continued)

*Primary Examiner* — Patrick Assouad
*Assistant Examiner* — Demetrius Pretlow
(74) *Attorney, Agent, or Firm* — Richard J. Coldren; Westinghouse Electric Company LLC

(57) ABSTRACT

The systems and methods of the invention pertain to analyzing steam generator tube data for the detection of wear. Further, the invention is capable of performing a comparison of current tube signal data to baseline or historic tube signal data, e.g., from previous and/or the first, in-service inspection of the steam generator. The systems and methods are automated and can generate results to show potential tube-to-tube contact wear areas as well as the progression of tube-to-tube gap reduction within a steam generator tube bundle. In certain embodiments, the invention is capable of comparing current and historical eddy current data to determine the difference that may be related to degradation or other interested phenomena, and of processing and trending historical comparison results to establish normal variance and detect abnormal variances.

8 Claims, 4 Drawing Sheets

(56) References Cited

U.S. PATENT DOCUMENTS

| | | |
|---|---|---|
| 6,823,269 B2 | 11/2004 | Junker et al. |
| 2003/0195710 A1 | 10/2003 | Junker et al. |
| 2005/0154564 A1* | 7/2005 | Le .................................. 702/189 |
| 2009/0150093 A1 | 6/2009 | Junker et al. |
| 2011/0089937 A1* | 4/2011 | Petrosky ....................... 324/220 |
| 2011/0172964 A1 | 7/2011 | Le |
| 2014/0012521 A1* | 1/2014 | Strizzi ............................ 702/58 |

OTHER PUBLICATIONS

International Preliminary Report on Patentability for PCT/US2013/063840 dated Apr. 23, 2015 (Forms PCT/IB/326, PCT/IB/373, PCT/ISA/237).

* cited by examiner

SYSTEMS AND METHODS FOR STEAM GENERATOR TUBE ANALYSIS FOR DETECTION OF TUBE DEGRADATION

CROSS REFERENCE TO RELATED APPLICATION

This application claims priority under 35 U.S.C. §119(e) to U.S. Provisional Patent Application Ser. Nos. 61/711,875, filed Oct. 10, 2012, entitled U-BEND ANALYSIS FOR DETECTION OF TUBE-TO-TUBE CONTACT WEAR AND TUBE-TO-TUBE PROXIMITY; 61/755,610, filed Jan. 23, 2013, entitled AUTOMATED HISTORY COMPARISON; and 61/755,601, filed Jan. 23, 2013, entitled AUTOMATED HISTORY TRENDING.

BACKGROUND

1. Field

This invention pertains in general to nuclear power plants and, more particularly, to systems and methods for evaluating the tubes of a steam generator of a nuclear power plant.

2. Description of Related Art

Nuclear power plants can generally be stated as comprising a reactor that includes one or more fuel cells, a primary loop that cools the reactor, and a secondary loop that drives a steam turbine which operates an electrical generator. Such nuclear power plants typically additionally include a heat exchanger between the primary and secondary loops. The heat exchanger typically is in the form of a steam generator which comprises tubes that carry the primary coolant and a plenum that carries the secondary coolant in heat-exchange relationship with the tubes and thus with the primary coolant.

As is also generally known, the tubes of a steam generator are subject to wear from mechanical vibration, corrosion, and other mechanisms. It thus is necessary to periodically inspect the tubes of a steam generator for wear in order to avoid failure of a tube which might result in nuclear contamination of the secondary loop, by way of example. Steam generator tube-to-tube contact wear generally is a concern in the nuclear industry. Both manual and automated processes are known to detect and address this concern. However, these known manual and automated processes have been shown to not be reliable. Methods of measuring tube-to-tube proximity (i.e., the spatial relationship between two adjacent SG tubes), a potential precursor for tube-to-tube contact wear, is cumbersome and also has been shown to not be reliable. Guidelines, analysis training and process changes have been implemented in the art with varying levels of success.

One method of inspecting the tubes of a steam generator involves the insertion of an eddy current sensor into one or more of the tubes and to receive from the eddy current sensor a signal which typically is in the form of a voltage and a phase angle. An analyst reviewing the signal data typically must possess a high degree of expertise in order to accurately ascertain from the signal data the current condition of the tubes of the steam generator. A typical steam generator might possess between three thousand and twelve thousand tubes, by way of example, with each tube being several hundred inches in length. Thus, the review of eddy current data can require the expenditure of large amounts of time by an analyst. While certain testing protocols may require the testing of fewer than all of the tubes of a steam generator, depending upon the particular protocol, the time in service, and other factors, the analysis of such data still requires significant time and expense.

Among the difficulties involved in the analysis of eddy current data is the determination of whether a signal is indicative of a possible failure of a portion of a tube or whether the signal is not indicative of such a failure. Each tube of a steam generator typically has a number of bends and a number of mechanical supports. In passing an eddy current sensor through such a tube, the signal from the eddy current sensor will vary with each mechanical support and with each bend, and the signal also will vary in the presence of a flaw such as a crack or a dent in the tube. As such, the difficulty in analysis involves the ability to determine whether a change in a signal from an eddy current is indicative of a known geometric aspect of a tube such as a bend or support, in which case further analysis of the signal typically is unnecessary, or whether the change in signal from the eddy current sensor is indicative of a crack or a dent, in which case further analysis of the signal typically is necessary.

To reduce the impact of the unwanted signals, the concept of combining data at different inspection frequencies, i.e., mixing, was implemented. By mixing data from different frequencies, an unwanted response can be minimized and a degradation response enhanced. The additional data provided by multi-frequency data acquisition coupled with the capability to eliminate unwanted signals places more information in the inspection results. This information is useful for assessing the reliability of the steam generators to operate during a fuel cycle and, for determining whether repairs should be performed in order to avoid costly and time consuming failures.

Outside Diameter Stress Corrosion Cracking (ODSCC) events that have occurred in operating nuclear power plants has increased the detection requirements of small and shallow signals. Such requirements pose significant challenges to the eddy current bobbin coil inspection technique which is commonly used for full length inspection of steam generator tubing. The traditional manual method of evaluating and comparing bobbin coil signals for change between inspections is time consuming and subjective. Alternate inspection techniques, such as rotating pancake coil probe and array coil probe, have shown to be costly and time consuming. Procedural control (analysis guidelines), analyst training and process changes have been introduced to address this issue but generally have not been proven to be entirely successful.

It is, therefore, an object of this invention to provide reliable systems and methods to analyze steam generator U-bend region bobbin coil data for accurate detection of tube-to-tube contact wear and tube-to-tube proximity. It is desired that these systems and methods are automated and the results can generate an illustration, e.g., map, to show the potential tube-to-tube contact wear areas as well as the progression of tube-to-tube gap reduction within a steam generator tube bundle. It is anticipated that the results obtained from these systems and methods and the illustration of the results will provide comprehensive steam generator repair solutions that will preclude failures and unplanned shutdowns that are time-consuming and costly.

It is another object of the invention to develop an automated process including signal processing techniques to identify and evaluate signals for change over a period of time to provide a consistent and reliable analysis of steam generator bobbin coil data from one in-service inspection to subsequent inspections.

It is another object of the invention to develop an automated process including trending of historical comparison results to establish normal variance and to detect abnormal variances.

SUMMARY

In one aspect, the invention provides a method of employing at least one eddy current sensor and at least one digital computing device to non-destructively assess a current condition of a number of tubes of a steam generator of a nuclear power plant. The method includes collecting at a first time with a digital computing device and using an eddy current sensor received in and advanced through each of at least some of the number of tubes a historic data set for each of at least some of the number of tubes; collecting at a second time with a digital computing device and using an eddy current sensor received in each of at least some of the number of tubes and advanced there through a current data set for each of at least some of the number of tubes; injecting at least a portion of the historic data set into a corresponding at least portion of the current data set with a digital computing device to form a merged data set; suppressing from the merged data set aspects that were present in the historic data set; and generating another data set representative of a change in condition of a tube of the number of tubes between the first time and second time.

In another aspect, the invention provides a method of employing at least one eddy current sensor and at least one digital computing device to non-destructively assess a current condition of a number of tubes of a steam generator of a nuclear power plant. The method comprises collecting at a first time with a digital computing device and using an eddy current sensor received in and advanced through each of at least some of the number of tubes a historic data set for each of at least some of the number of tubes; collecting at a second time with a digital computing device and using an eddy current sensor received in each of at least some of the number of tubes and advanced there through a current data set for each of at least some of the number of tubes; measuring noise window of the historical data set to determine a historical noise baseline; storing the historical noise baseline in the digital computing device; measuring noise window of the current data set to determine a current noise baseline; storing the current noise baseline in the digital computing device; comparing the historical noise baseline and the current noise baseline to determine a difference; and identifying a region of a baseline shift based on the difference to show potential tube to tube contact or long taper wear.

In another aspect, the invention provides a method of employing at least one eddy current sensor and at least one digital computing device to non-destructively assess a current condition of a number of tubes of a steam generator of a nuclear power plant. The method comprises collecting at a first time with a digital computing device and using an eddy current sensor received in and advanced through each of at least some of the number of tubes a historic data set for each of at least some of the number of tubes; collecting at a second time with a digital computing device and using an eddy current sensor received in each of at least some of the number of tubes and advanced there through a current data set for each of at least some of the number of tubes; measuring a signal of interest using the historical data set and recording at least one signal characteristic selected from the group consisting of signal amplitude, phase, pattern, signal width, and signal area; storing the at least one signal characteristic in database; measuring a signal of interest using the current data set and recording at least one signal characteristic selected from the group consisting of signal amplitude, phase, pattern, signal width, and signal area; storing the at least one signal characteristic in database; generating a trending plot comparison between the at least one signal characteristic for the historical and current data sets to determine variances there between; determining a normal variances based on the historical data set to determine a normal variance zone; and determining an abnormal variance based on the current data set if the comparison is different than the normal variance.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
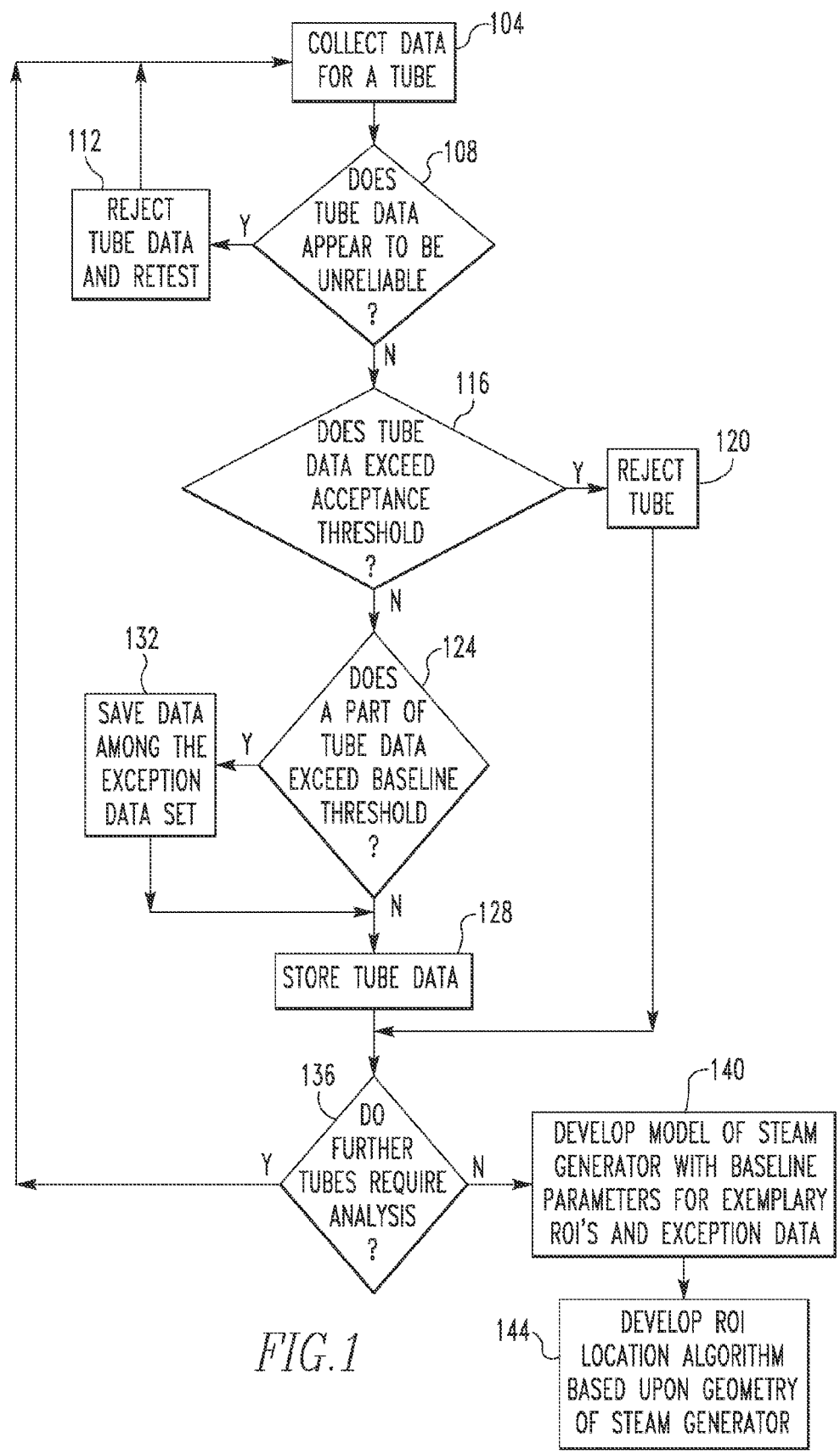
FIG. 1 is a flowchart depicting certain aspects of the invention.

The systems and methods of the invention pertain to analyzing steam generator U-bend region bobbin coil data for the detection of tithe-to-tithe contact wear. Also, the systems and methods can detect and measure undesirable tube-to-tube proximity conditions that may cause future tube-to-tube contact wear issues. The invention includes several advanced signal processing techniques that remove the U-bend region anti-vibration bar structure interference upon the bobbin coil signal). Further, the invention is capable of performing a comparison to signals from baseline data obtained from previous, e.g., the first, in-service inspection of the steam generator. Any change in data, e.g., bobbin coil signals, that exhibit flaw-like characteristics are subjected to additional evaluation or testing with an alternate inspection technique. The systems and methods are automated and can generate the results in such a form, e.g., a map, to show potential tube-to-tube contact wear areas as well as the progression of tube-to-tube gap reduction within a steam generator tube bundle. This complete steam generator tube-to-tube contact wear and tube bundle proximity analysis provides information necessary to devise and develop comprehensive repair solutions. The systems and methods of the invention are capable of processing and trending historical comparison results to establish normal variance and to detect abnormal variances.

In general, the invention includes performing a total signal and noise analysis from baseline or first in-service inspection, determining straight section, support, and bend tube information, storing this tube information, creating processed channels with the structure interfering signals removed to allow a true measurement of the baseline signal, and storing the baseline true measurement in a database. The total signal and noise analysis can be performed using suitable software, such as but not limited to Real Time Automated Analysis (RTAA). RTAA is an automated analysis process which is generally known in the art for use in inspecting steam generator tithes for degradation. A true measurement of the baseline signal can be accomplished using rolling noise window measurement. In certain embodiments, this concept and method are used to generate a baseline inspection of tube U-bends and tube supports and transitions to determine wear. In other embodiments, this concept and method is used to generate a baseline inspection of straight length tube sections to determine whether the tube is bent such that it may contact adjacent tubes.

During subsequent steam generator tube inspections, a total signal and noise analysis, e.g., current, is performed using RTAA and a true measurement of the U-bend signal, e.g., current, is obtained using rolling noise window measurement. This current data is then merged and compared with previous or historical data stored in the database, e.g., the baseline or first in-service inspection data, to identify any changes. For each current tube signal, the same tube signal information from the baseline database is examined for comparison.

In certain embodiments, the baseline and current tube inspection data each can be obtained in accordance with the following process. An eddy current sensor is received within the interior of an elongated tube of a steam generator and is passed through the interior of the tube along the longitudinal extent thereof. Longitudinal movement of the sensor can be performed manually, although it can also advantageously be performed by a robotically-controlled advancement mechanism that advances the eddy current sensor at a controlled rate and that is capable of providing a data stream component representative of the longitudinal distance of the eddy current sensor along the tube at any given time. Other data streams from the eddy current sensor typically comprise a voltage component that characterizes amplitude and another component that characterizes a phase angle. Although many methodologies can be employed for the storage and analysis of such data streams, one methodology involves the storage of voltage and phase data at given points along the longitudinal length of a tube. Typically, thirty data points per inch are collected and stored, but other data distributions and densities can be employed without departing from the present concept.

As is generally understood, a typical steam generator includes a plenum that encloses perhaps four thousand to twelve thousand individual tubes that each comprise a hot leg and a cold leg that pass through a tube sheet, which is itself a slab of metal that is typically twenty or more inches thick. Each tube may be several hundred inches long and have either a single U-bend or a pair of elbow bends, although other geometries can be employed without departing from the present concept. Each such tube typically additionally includes twenty to thirty physical supports of differing geometries. During initial manufacture, the hot and cold legs of each tube are assembled to the tube sheet by receiving the two ends of the tube in a pair of holes drilled through the tube sheet and by hydraulically bulging the ends of the tube into engagement with the cylindrical walls of the drilled holes.

While the geometry of each tube of a steam generator typically is different from nearly every other tube of the steam generator, the overall construction of the steam generator enables generalizations to be made with regard to the geometry of the tubes as a whole. That is, each tube can be said to include a pair of tube sheet transitions at the ends thereof which typically are characterized by an eddy current sensor voltage on the order of thirty (30.0) volts. Between the two tube sheet transitions are various straight runs, supports, and bends. The typical eddy current voltage for a straight section of tube is 0.05 volts, and the typical voltage for a bend of a tube is 0.1 volts. A typical voltage for a support may be 0.2 volts, hut various types of supports can exist within a given steam generator, all of which may produce different characteristic voltages.

Advantageously, however, the various arrangements of straight sections, supports, and bends as a function of distance along a tube are of a limited number of permutations within any given steam generator. As such, a location algorithm is advantageously developed from the known geometry of the steam generator and the historic data that can be collected from the steam generator, wherein an input to the algorithm of a series of voltage and distance values can identify a particular region of interest (ROI) of a tube that is under analysis. That is, the wear that is experienced by a tube often can occur at a tube sheet transition, at a location of attachment of a tube to a mechanical support, at a transition between a straight section and a bend in a tube, or at other well understood locations. The various segments of a given tube can be divided into various regions of interest (ROIs) which can be identified during data collection with a high degree of accuracy based upon the details of the steam generator geometry that are incorporated into the location algorithm. As such, by inputting voltage, phase, and distance data into the location algorithm, the location algorithm can identify a specific segment and thus, physical ROI of the tube being analyzed.

The invention can also be said to include the development of a model for the steam generator that includes baseline parameters such as voltage and phase for each of a plurality of exemplary ROIs that exist in the particular steam generator. Advantageously, and as will be set forth in greater detail below, the model additionally includes exception data for particular ROIs of particular tubes that have voltage and/or phase angle parameters that would exceed the baseline parameters of the corresponding ROI of the model but that are nevertheless acceptable, i.e., the signals from such ROIs are not themselves indicative of flaws that require further evaluation by an analyst.

The baseline parameters for the various exemplary ROIs of the model can be established in any of a variety of ways. In the exemplary embodiment described herein, the various baseline parameters for the various exemplary ROIs of the model are established based upon theoretical evaluation of tubes and their ROIs, as well as experimental data based upon eddy current analysis of actual tubes and their physical ROIs. The direct physical analysis of tubes such as through the collection of eddy current data of individual tubes of a steam generator advantageously enables the collection of data with respect to typical ROIs that can be employed in establishing baseline parameters for exemplary ROIs of the model. Such direct physical analysis of tubes can additionally be employed to collect data that is later stored as exception data for particular ROIs of particular tubes.

Additionally and advantageously, such direct collection of eddy current data during the initial manufacture of a steam generator can enable an initial evaluation of each tube to assess whether the tube should be rejected or whether the data appears to be unreliable and should be recollected. A tube may be rejected if the data suggests that it is defective in manufacture. On the other hand, the data may need to be recollected if it appears that the eddy current sensor was functioning improperly or if other data collection aspects appear to be erroneous or unreliable.

FIG. 1 generally depicts an exemplary methodology for the collection of tube data which enables the development of a model of a steam generator and the development of a location algorithm that is based upon the geometry of the steam generator. Processing begins, as at 104, where eddy current data is collected for a given tube of the steam generator. As mentioned herein, the data stream typically will include components of voltage, phase, and distance, all of which can be detected as a continuous signal or as a discrete set of data points along the length of the tube.

In FIG. 1, processing continues at 108, where it is determined whether the data derived from the eddy current sensor signal is potentially unreliable. For instance, if the data suggests a possible data collection error, processing continues as at 112, where the tube data is rejected, and the tube is retested. Processing thereafter would continue, as at 104. However, if at 108 the data is not determined to be unreliable, processing continues, as at 116, where it is determined whether the tube data derived from the eddy current signal exceeds an acceptance threshold, such as would indicate that the tube itself is mechanically or otherwise defective. In the event that the data exceeds an acceptance threshold, the tube is rejected, as at 120.

If the tube data does not exceed the acceptance threshold at 116, processing continues, as at 124, where it is determined whether any portions of the tube data exceed what should theoretically be the baseline parameters of that portion of the tube, i.e., the baseline parameters for the corresponding exemplary ROI of the model of the steam generator. By way of example, it may be determined that the physical ROI of the tube that is under analysis includes a physical support and the eddy current sensor is indicating a voltage of 0.4 volts. While an analyst may determine that the voltage that would typically be expected for such an ROI is 0.2 volts, the analyst may nevertheless determine that the particular physical ROI is acceptable and that the voltage of 0.4 volts is an acceptable anomaly. In such a circumstance, the data for the particular ROI for this particular tube will be saved, as at 132, as a portion of an exception data set. In this regard, it is reiterated that the tube or its data would already have been rejected, as at 112 or 120 respectively, if the data for the aforementioned ROI suggested that the ROI would be unacceptable.

Referring to FIG. 1, processing continues from both 124 and 132 onward to 128 where the tube data is stored in a data set. It is then determined, as at 136, whether further tubes require eddy current analysis as set forth above. If further tubes await testing, processing continues, as at 104, with a new tube. Otherwise, processing continues, as at 140, where the model of the steam generator is developed with a set of baseline parameters for each of a plurality of exemplary ROIs. The model further includes the aforementioned exception data for one or more particular ROIs of one or more particular tubes. It is understood that the inclusion as at 140 of the development of the steam generator model at this particular location within the exemplary methodology is intended to be merely an example of a point at which a model of the steam generator can be developed. It is understood that with analytical methods, at least an initial model of the steam generator can be developed, with the experimental collection of tube data from 104 through 132 being supplied to the model to provide refinement of the model and to provide exception data. It thus is understood that the model of the steam generator can be developed in whole or in part at any time depending upon the data and the analysis that are available.

Referring to FIG. 1, processing continues to 144 where the location algorithm which identifies various ROIs can be developed based upon the geometry of the steam generator and other factors. As was mentioned elsewhere herein with respect to the development of the model of the steam generator, the location algorithm can likewise be developed in whole or in part at any time depending upon the analytical and experimental data that is available in the development process depicted generally in FIG. 1. When completed, the location algorithm advantageously can receive a data stream from an eddy current sensor within the tube of the steam generator and can employ the voltage, phase, and distance data components to identify any of a variety of exemplary ROIs that are stored within the model of the steam generator. That is, the location algorithm can employ the eddy current signal within a tube of the steam generator to identify a particular segment of the tube and thus a physical ROI of the tube, and the location algorithm can additionally identify from the model that was developed of the steam generator a corresponding exemplary ROI and its baseline parameters for comparison with the eddy current signal that is being collected from the physical ROI.

Figure 2:
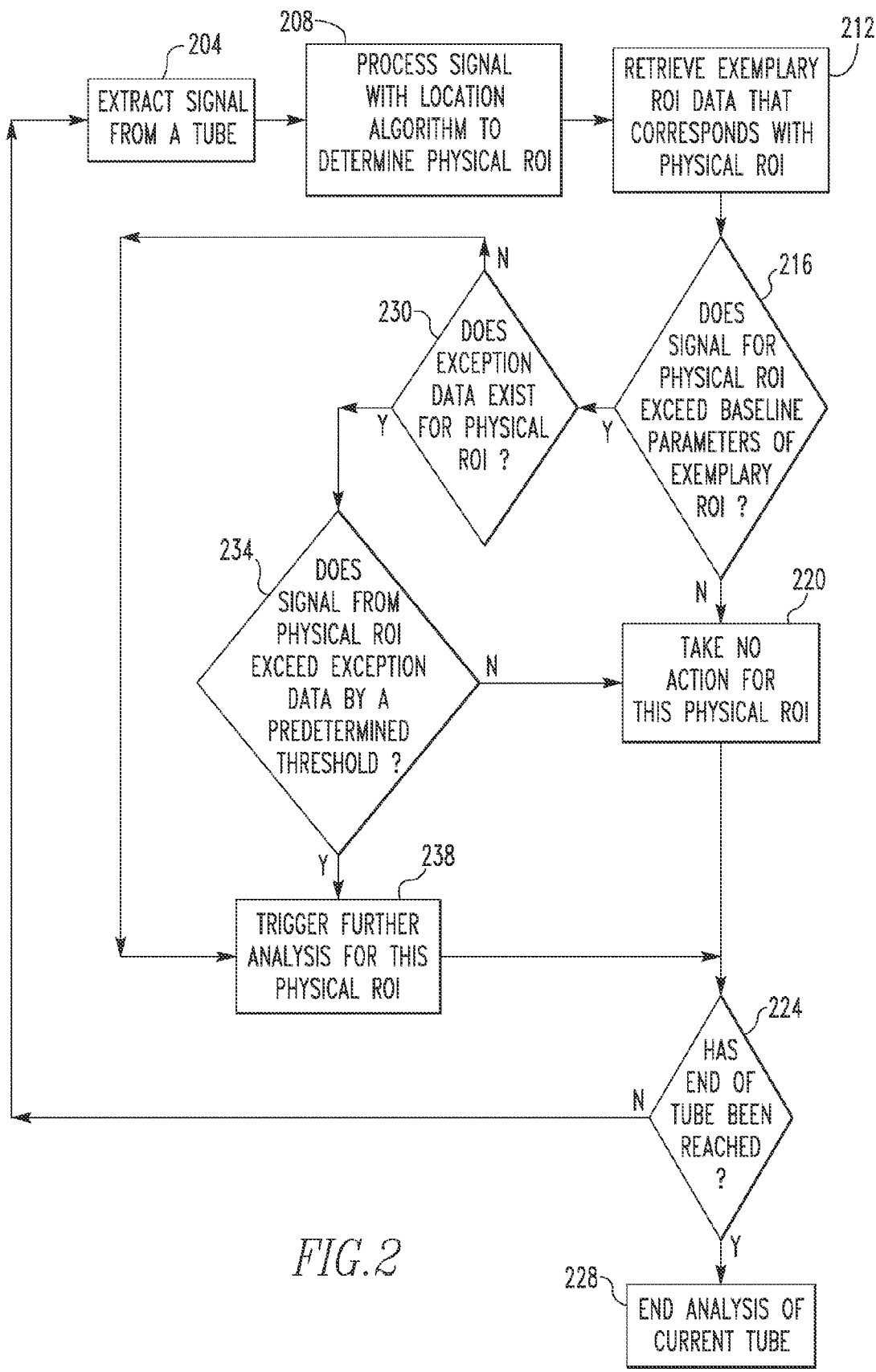
FIG. 2 is a flowchart of steps included in the method of this invention.

The testing of the tithes of a steam generator is depicted in an exemplary fashion in FIG. 2. It is understood that the operations depicted generally in FIG. 1 typically will occur at a first time and will be in the nature of a historic data set. The operations occurring in FIG. 2 typically occur at a second, subsequent time and may more likely be directed toward current or present testing of a steam generator. Processing begins, as at 204, where a signal is extracted from a tube of the steam generator. The signal from the eddy current sensor is processed with the aforementioned location algorithm, as at 208, to determine the physical ROI that is the source of the signal that is being collected from the tube under analysis. The location algorithm then employs, as at 212, the signal from the eddy current sensor to retrieve from the model an exemplary ROI that is determined to correspond with the physical ROI that has been located by the location algorithm. It is then determined, as at 216, whether the signal data for the physical ROI exceeds the baseline parameters of the exemplary ROI from the model that was identified and retrieved at 212. If it is determined at 216 that the eddy current signal for the physical ROI does not exceed the baseline parameters of the exemplary ROI, processing will continue, as at 220, where no further action will be taken with respect to this particular physical ROI. That is, no additional analysis will be triggered for this particular physical ROI, thereby avoiding the need for an analyst to perform any evaluation with respect to this physical ROI.

It is then determined, as at 224, whether the end of the tube under analysis has been reached. If so, the analysis of the current tube ends, as at 228. Another tube can then be analyzed. However, if the end of the tube is determined at 224 to not be reached, processing continues, as at 204, where the eddy current signal is continued to be extracted from the tube under analysis.

The aforementioned baseline parameters of the various exemplary ROIs of the model can be developed in any of a variety of fashions. Most typically, the baseline parameters will be developed with the use of theoretical data and experimental data, as suggested above. For instance, the typical eddy current voltage that one might expect to detect from a straight section of a tube is 0.05 volts, and the data collection effort depicted generally in FIG. 1 might demonstrate, by way of example, that the tested voltage values for each straight segment of each tube is 0.08 volts or less. As such, the baseline voltage for an exemplary ROI that corresponds with a straight section of a tube might be established 0.1 volts. This would enable all physical ROIs that are straight sections of tubes to, in their original condition, not exceed the baseline parameter of 0.1 volts and thus not trigger the need for further analysis, as at 220.

Similarly, the typical eddy current sensor voltage that one might expect from a curved section of a tube is 0.1 volts, and the baseline parameter for experimental ROIs of bend segments of each tube might be established at 0.2 volts. Physical supports typically generate an eddy current voltage of 0.2 volts, so the baseline parameter for a physical support ROI might be established at 0.3 volts. Such baseline parameters typically will be based upon the various specifications of the steam generator and the nuclear power plant, along with theoretical and experimental data regarding the steam generator. It is understood, however, that the baseline parameters typically will be selected such that an eddy current sensor signal that exceeds a baseline parameter is worthy of further evaluation by an analyst, assuming that applicable exception data for the particular physical ROI does not already exist in the model. That is, the baseline parameters desirably will be selected such that no further action is triggered when the eddy current sensor signals are below that which should reasonably trigger further analysis of the particular physical ROI. It is understood, however, that various methodologies may be employed for establishing the baseline parameters of the exemplary ROIs without departing from the present concept.

It is also noted that the baseline parameters can include voltages, phase angles, pattern data, and any other type of characterization of an exemplary ROI that may be appropriate. The degree of sophistication of the baseline parameters is limited only by the ability to collect and analyze data regarding the tubes. As such, the baseline parameters of an exemplary ROI can be determined to be exceeded if any one or more of the various parameters in any combination are exceeded by a signal without limitation. Additionally or alternatively, the baseline parameters could have an even greater degree of sophistication wherein certain combinations of parameters need to be exceeded in a certain fashion for the system to trigger the need for further analysis, by way of example.

On the other hand, if it is determined, as at 216, that the signal for the physical ROI exceeds in some fashion the baseline parameters of the identified corresponding exemplary ROI, processing continues, as at 230, where it is determined whether exception data exists for the physical ROI that is under analysis. As mentioned elsewhere herein, the exception data advantageously will be a part of the model of the steam generator. If such exception data is determined at 230 to exist, processing continues, as at 234, where it is determined whether the signal from the physical ROI exceeds the exception data by a predetermined threshold. That is, it is not expected that the physical ROI that is the subject of the exception data will remain unchanged during the life of the steam generator, and rather it is expected that the physical ROI might degrade over time due to wear, corrosion, etc. Since the physical ROI has already been determined at the time of taking the historic data set to have a signal which exceeds the baseline parameters that would otherwise be expected from a similar ROI, the threshold that is already built into the baseline parameters is unlikely to be useful evaluating the particular physical ROI that is the subject of the retrieved exception data. As such, a separate threshold is established based upon various factors which, if exceeded by the present signal from the physical ROI, will trigger further analysis as at 238, of this particular physical ROI. Such further analysis likely will be manual evaluation by an analyst. On the other hand, if it is determined at 234 that the signal from the physical ROI fails to exceed the retrieved exception data by the predetermined threshold, processing continues, as at 220, where no further action is taken for this particular physical ROI. Further evaluation by an analyst is also triggered, as at 238, if it is determined, as at 230, no exception data exists for this particular physical ROI.

It is noted that an additional notification can be triggered if the baseline parameters of the exemplary ROI are exceeded by a significant amount, or if the predetermined threshold for the exception data is exceeded by a significant amount, in order to alert an analyst that an increased level of attention should be directed to a particular physical ROI, for example. In the exemplary embodiment depicted herein, for instance, further analysis is triggered if either the baseline parameters of the exemplary ROI or the predetermined threshold of the exception data is exceeded in any fashion. However, an additional notification can be generated if the signal exceeds the baseline parameters or the predetermined threshold of the exception data by 25%, by way of example. It is understood that any type of criteria can be employed to trigger such heightened further analysis.

It therefore can be seen that the eddy current data that is collected from a tube under analysis is evaluated using the model that includes exemplary ROIs with baseline performance parameters and further includes exception data for ROIs of particular tubes, with the result being the triggering of further analysis such as evaluation by an analyst only in specific predefined circumstances such as would occur at 238. As such, the manual evaluation effort that is required of an analyst using the exemplary methods set forth herein is greatly reduced compared with known methodologies.

It is noted that the exemplary method depicted generally in FIG. 2 envisions a real-time automated analysis system wherein a signal that is collected from a tube is input directly into the location algorithm and is evaluated as it is collected. It is understood, however, that different methodologies may be employed. For instance, the data from one or more tubes can be collected and stored and then evaluated as a whole rather than being analyzed on a real-time basis. Other variations can be envisioned that are within the scope of the present concept.

Figure 3:
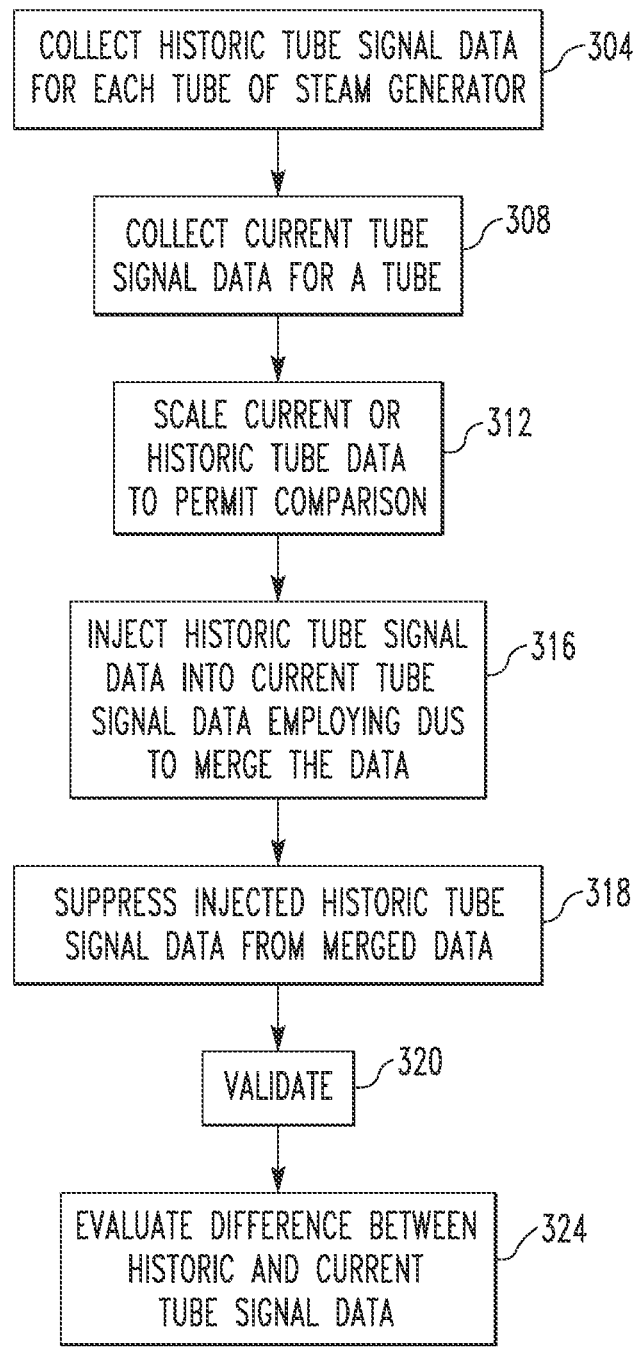
FIG. 3 is a flowchart depicting certain other aspects of the invention.

FIG. 3 generally depicts an exemplary methodology for analyzing signals of interest collected from regions or areas of interest of tubes in a steam generator that is undergoing analysis. As such, another aspect of the invention is to collect historic tube signal data for each tube, e.g., region or area of interest of a tube of a steam generator, as at 304, and employ the historic tube data for use at a later time in comparison with tubes, e.g., region or area of interest of a tube of a steam generator that is under analysis after a period of use. Advantageously, the historic data shares certain aspects with current collected data. The method advantageously merges the historical and current signal data, and suppresses from the current signal data any aspects that were also present in the historic tube data in order to generate an improved simpler signal that is indicative of a change in condition of the area or region of a tube under analysis. The historic tube signal data can be taken at the time of manufacture of the steam generator or can be taken at a later time, such as during an in-service inspection of a steam generator.

The historic tube signal data that is collected at 304 during manufacture or in-service inspection of a steam generator is then stored for future retrieval and comparison with subsequently collected data during a current testing operation. That is, current tube signal data is collected, as at 308, for a given tube of a steam generator. The historic tube data for the same tube is retrieved. It is typically the case that some type of scaling with respect to either the current data or the historic data will occur, as at 312, to permit comparison. By way of example, it may be necessary to reduce or increase or otherwise manipulate all of the values of either the current or historic data sets since different eddy current sensors or other instrumentation were employed to take both sets of data or because of other differing operating parameters between the eddy current sensors employed to take the historic and the current tube data. Other types of scaling may be necessary if the data points of the historic tube data do not match sufficiently with the data points of the current tube data. As mentioned elsewhere herein, data may be taken at thirty locations per inch, although forty-five locations per inch may likewise be employed, as can other data signal densities. Still other scaling may be required if the direction of movement of the eddy current sensor is different between the historic data and the current data. For example, the historic data may have been based upon longitudinal movement of an eddy current sensor in a direction from the tube sheet toward the tube sheet transition, whereas the current data may involve an eddy current sensor that is moving in a direction from the tube sheet transition toward the tube sheet. Regardless of the nature of the historic and current tube data, scaling or other mathematical manipulations may be performed at 312 to permit comparison between the two.

The historic tube signal data is then injected into the current tube signal data, as at 316. That is, these two data sets, i.e., the historic and the current tube data, are combined to form a merged tube signal data set. The merged data set is subjected to a suppression step. The injected historic tube data of the merged data set is suppressed, as at 318. The suppression process employs the ANSER ALFS (Axial Look Forward Suppression) software that is licensable from Westinghouse Electric Company, LLC, Cranberry Township, PA. The ANSER software suppresses identified signals (e.g., tube sheet transition) and enhances degradation signal (e.g., ASME 20% flaw). Other suppression techniques and software may be used such as, but not limited to, simple mix. However, in certain embodiments wherein multiple year comparisons are to be performed, the ALFS is preferred because it has this capability. The suppression output is validated, as at 320. Validation provides verification of suppression of common mode signal not to exceed a pre-determined voltage (such as 0.5 V) and enhancement does not distort the sample defect as well as preserves its phase and voltage (e.g., 20% hole signal at greater than 4V and more than 140 degrees) and thus, increases confidence in the ability of the process to accurately detect degradation. As a result, a new signal is generated which is representative of the change in condition of the tube, e.g., area/signal of interest, that is under analysis between the time at which the historic tube data was collected, such as at the time of manufacture or during an in-service inspection, and the time at which the current tube data is collected.

The injection and suppression of the tube data, as at 316 and 318, can be performed by employing suitable software, such as but not limited to Data Union Software (DUS) which is licensable from Westinghouse Electric Corporation, LLC, Cranberry Township, PA. The DUS software generally provides for combining, e.g., merging, mixing or injecting, two data sets, e.g., historic and current tube signal data, to produce a data set that is a combination of the two data sets. Employing DUS provides advantages over prior art software, such as but not limited to, the ability to: (i) process historical and current data sets that may be collected using different instruments and operating parameters; (ii) subject both the historic and current data sets to a common mode data noise environment in order to suppress any common mode signal; (iii) perform suppression on merged data to increase the speed and efficiency of the process, and (iv) apply in a cumulative manner to permit multiple sets of historic data to be compared with current data with efficiency and high accuracy.

Figure 4:
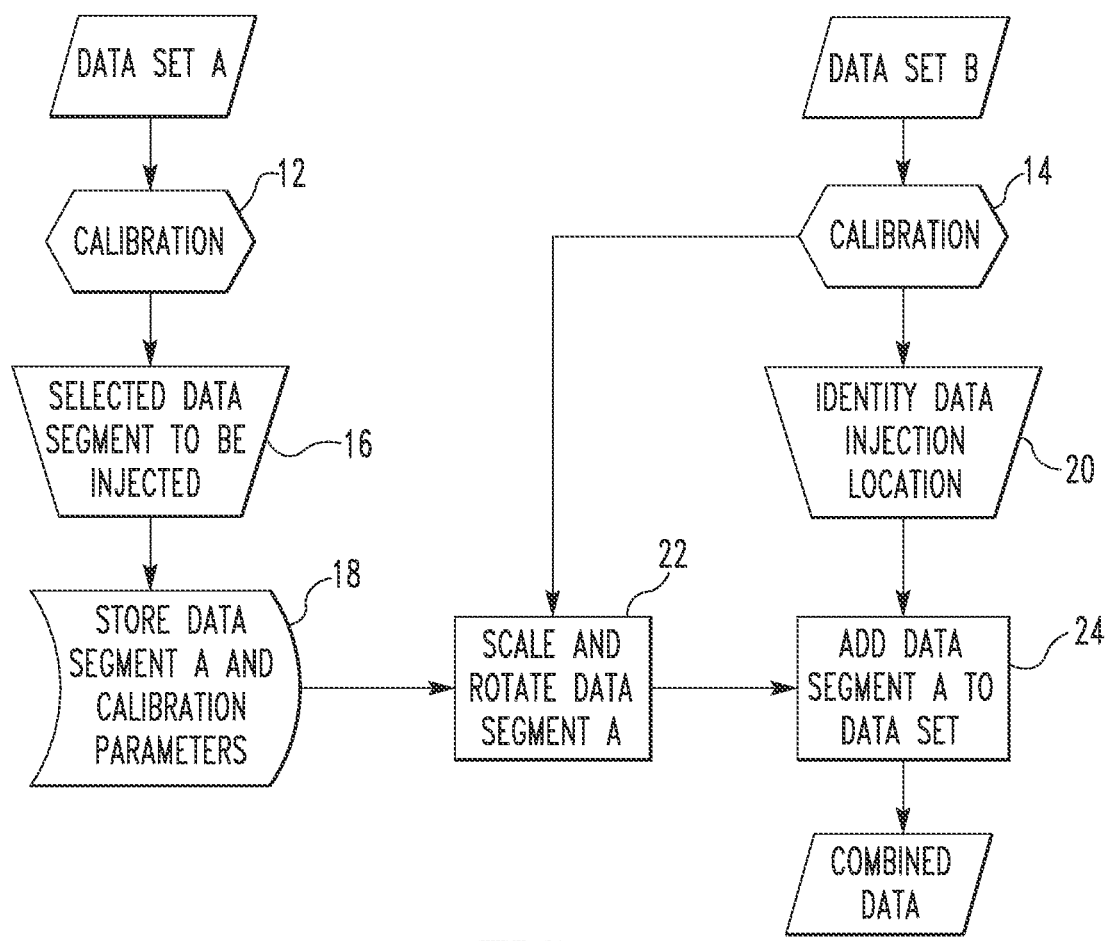
FIG. 4 is a flowchart depicting certain other aspects of the invention.

A flow chart of the overall data combination process of this invention is shown in FIG. 4. Referring to FIG. 4, the first steps 12 and 14 in the data injection process are to define the calibration or normalization parameters for each Data Set A and B, wherein A represents historic tube sheet transition data and B represents current tube sheet transition data. Preferably, at least one of the standard holes or notches in a calibration standard used for this purpose should be identical for both data sets. If they are not identical, mathematical models can be used as a basis for interpolation of one or the other of the data sets. The calibration standard is a specimen created in accordance with the ASME code. Each of the data sets is then calibrated so that the reference discontinuity response for the two data sets, A and B, is identical. For bobbin coil eddy current data, this can be accomplished by setting the voltage of the 20% holes, i.e., 20% through-wall flaw, to 4 volts and the phase of the through-wall hole to a 40° rotation. For rotating probe data, the through-notch in the calibration standard can be used to set the phase and amplitude. For most applications, it can be assumed that the accuracy of the standard is sufficient so that cross calibration of the standards is not required.

After the calibration parameters are established, the segment of data from data set A to be inserted into data set B is selected and stored in step 16, shown in FIG. 4. In the system, this is accomplished by superposition of the calibration signal into a duplicate segment of current data. This data then can be used for enhancement of historic comparison, as well as validation to ensure the result of comparison has not distorted the injected calibration signal. The data segment A along with the calibration parameters for that segment determined in step 12 is then stored in a file. Multiple segments from the same tube or specimen can be stored and each identified with a ROW/Col. and sequence number as represented by step 18 in FIG. 4.

Referring to FIG. 4, after the segments of interest have been identified, the data set B in which the segment is to be inserted is read into the machine. The location where the segment is to be inserted is chosen in step 20. In the DUS system, this is accomplished by duplicating a segment of current data in the free span that is free of structure signal or other anomalies. Once the segment A data is selected, the appropriate calculations are made in step 22, based upon the calibration parameters, to rotate and scale the segment A data so that it has the same calibration factors as data set B. The thus normalized segment A data is then added to the displayed data set in step 24 shown in FIG. 4. To display the results with the DUS system, data set B must be reread into the machine. This process can be repeated with different sets of data from different years thus, permitting historical comparison of multiple years.

In the foregoing embodiment, the segment A data is added into the displayed data. If desired, the segment A data could equally well replace some of the displayed data in set B. Furthermore, since the data set that is being displayed is the file that is modified, it is important that the combination process take place on a copy of the data and not the original file. Once the combination process is complete, the new data set can be manipulated in the same way as any other data set. No knowledge of the data combination process is retained in the combined file.

In certain embodiments, it may be desirable to amplify one or more portions of the new signal that is generated. Such an amplified signal would emphasize those aspects of the new signal that would be even more indicative of a change in the condition of the tube sheet transition between the time the historic data was collected and the time that the current data is collected.

The signal is then submitted, as at 324, for evaluation. Such evaluation may be performed automatically or may be performed manually by an analyst. It is then determined whether any additional tubes of the steam generator require analysis with respect to their tube region. If further tubes require analysis, processing continues. Otherwise, processing ends.

In this regard, it is understood that the aforementioned tube analysis can be performed as a part of the analysis depicted generally in FIG. 2 or can be performed separately. In this regard, the historic tube data that was collected at 304 potentially can be saved as part of the model of the steam generator, particularly as a special part of the exception data set. As such, it may be possible to completely analyze a tube from one tube sheet transition through its longitudinal extent and to its opposite tube sheet transition using the teachings herein. As mentioned elsewhere herein, however, it is possible to analyze the tube sheet transitions separately from the other portions of the tubes, as may be desired.

As previously mentioned, the analysis methodology depicted in FIG. 3 is applicable to signals of interest collected from regions or areas of interest of the tubes of a steam generator. Thus, the methodology can be used throughout the steam generator tube to analyze dents, supports, straight length segments, tube sheets, transitions, and the like. In certain embodiments, the methodology is useful in analyzing tube sheet transition regions. Due to the thickness of the tube sheet, the eddy current data that is collected from a tube in the tube sheet transition region typically is of a voltage far in excess of any of the baseline parameters of any of the exemplary ROIs. Moreover, the variation in eddy current voltage from one tube sheet transition to another is also far in excess of any baseline parameter of an exemplary ROI. For instance, and has been mentioned elsewhere herein, the eddy current voltage for a tube sheet transition might be on the order of thirty (30.0) volts. The eddy current voltage of another tube sheet transition might be 25.0 volts, and that of another tube might be 35.0 volts. Since the eddy current voltages at tube sheet transitions are one or more orders of magnitude greater than any voltage that would be generated in other portions of the tube, i.e., portions other than the tube sheet transition, the method depicted in FIG. 3 is useful to facilitate the analysis of signals collected from tube sheet transitions of a steam generator that is undergoing analysis. In general terms, it is understood that the eddy current signals from tubes in the tube sheet transition area of a steam generator are of a voltage that is sufficiently high that the portion of the eddy current signal which might indicate a possible flaw, i.e., the signal of interest, which might be on the order of 0.1 volts, is far too small in comparison with the overall eddy current signal to be easily detected or evaluated.

It is also noted that the teachings employed herein can be applied in a cumulative fashion to permit multiple sets of historic data to be compared with current data. That is, historic data can be taken at a first time, such as at the time of manufacture of a steam generator or at an in-service inspection, and such historic data can be employed during a subsequent evaluation of the steam generator tubes. The data that is developed during such a subsequent evaluation may then be stored as a second historic data set. Both historic data sets can then be compared with data that is collected during a further inspection of the steam generator to enable the change in the condition of various tubes to be charted as a function of time over the course of several inspections that occur at several different times. Other uses of the data can be envisioned.

It is understood that the analysis described herein can be performed on a digital computer or other processor of a type that is generally known. For instance, such a computer might include a processor and a memory, with the memory having stored therein one or more routines which can be executed on the processor. The memory can be any of a wide variety of machine readable storage media such as RAM, ROM, EPROM, EEPROM, FLASH, and the like without limitation. The signal from the eddy current sensor might be received by an analog-to-digital converter which provides a digital input to the computer for processing and storage of the signals. The historic and current data can be stored on any such storage media and can potentially be transported or transmitted for use on other computers or processors as needed.

In general, the invention includes, but is not limited to, the following features and embodiments. The absolute measurement from current outage and the difference of the current measurement from baseline (or first in-service inspection) data can be generated to create a steam generator tube bundle to assess tube-to-tube contact wear. Sudden shifts in the spatial relationship between two or more adjacent steam generator tubes based on comparison of baseline and current measurements can indicate tube proximity issues.

U-bend signal information from two or more outages can be normalized for each steam generator tube and overlaid to measure differences from the baseline measurement. In certain embodiments, the recall of data from one or more previous outages can be obtained using appropriate software. One or more process channels can be created for this information. Data difference channels can be created with low pass filter to remove sudden anomaly change from the normalizing process and to provide trending analysis of the tube bundle proximity progression.

An automated history comparison process can be employed. The process includes collecting a current non-destructive examination signal; identifying a historical inspection signal from a previous inspection, for example and without limitation, using Enhanced Automated History Address (EAHA) and full data recall (FDR); and measuring and storing current inspection signal characteristics and historical inspection signal characteristics in a database.

The signal characteristics of the current and previous measured inspection data stored in the database are defined as follows:
  Signal amplitude and phase;
  Multiple signal measurement modes, such as volts peak-to-peak (Vpp), volts max rate (Vmr) and the like;
  Multi-channel comparison;
  Multiple bobbin coil responses, e.g., differential or absolute;
  Other signal characteristic include but are not limited to signal shape, signal width and signal area; and
  Signal superposition from other design conditions, i.e., support structure signal, or from service induced conditions, such as sludge pile deposits or denting.

The automated history comparison process further includes processing and aligning the historical signal for comparison to the current signal. The processing can include transformation and scaling of the data to match the data density and inspection direction. The transformation also includes but is not limited to amplitude and phase adjustment due to differences in inspection tester configuration and tester excitation modes (multi-plexed vs. simultaneous injection). Signal segments that can be compared include, among others:
  Noise exceedances, for example, Free-span Hot Leg (FHL) or Free-span Cold Leg (FCL); and
  Region of Interest (ROI) comparison, for example, full support, Support Edge Hot (SHE) and Support Center Hot (SCH).
  The comparison of historical and current signals can be made from signal subtraction, ROI mixing (SP edge mix or SP center mix).

The automated history comparison process also includes storing the comparison results in a database. In the automated history comparison process, accurate historical signal identification is essential to correct and effective comparison. The comparison algorithm used balances between preserving a degradation signal and suppressing a common mode signal.

An automated process utilizing a high performance database to record and evaluate multiple signal comparison results over several years is provided. A technique that establishes normal variance based on observations of earlier years data is utilized. An automated history trending process can search for and identify variances that are above a normal variance threshold.

An automated history trending process can include collecting non-destructive examination results and producing a trending curve for various comparison results including but not limited to the following:

Volt, phase;

Signal area, signal width;

Correlation with other ROIs in the same steam generator Ube or in tubes with similar properties, e.g., Sigma tube or adjacent tube; and Noise exceedance.

The automated history trending process can further include storing the trending curve and slope in a database, and establishing the slope and standard deviation of normal variance for early service years, e.g., first, $2^{nd}$ and $3^{rd}$ in-service inspection comparisons. Furthermore, the automated history trending process includes querying the database to detect sudden slope change with current and prior data comparison; and mapping the query results to a tube sheet map to highlight regions of concern and correlate problem areas in the steam generator tube bundle.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the fill breadth of the appended claims and any and all equivalents thereof.

What is claimed is:

1. A method of employing at least one robotically controlled eddy current sensor and at least one digital computing device to non-destructively assess a current condition of a number of tubes of a steam generator of a nuclear power plant, the method comprising:

collecting at a first time with a digital computing device and using an eddy current sensor received in and robotically advanced through each of at least some of the number of tubes, a historic data set at a U-bend region for each of at least some of the number of tubes, including signals generated by geometric aspects of the U-bend region;

collecting at a second time with a digital computing device and using an eddy current sensor received in and robotically advanced through each of at least some of the number of tubes, a current data set at a U-bend region for each of at least some of the number of tubes, including signals generated by U-bend structures;

combining at least a portion of the historic data set into a corresponding at least portion of the current data set with a digital computing device, comprising;

calibrating tube data signals in each of the historic data set and the current data set;

selecting one or more segments of interest in the historic data set;

merging a calibrated tube data signal corresponding to each of the one or more segments of interest of the historic data set into a corresponding location in a duplicate copy of the current data set; and suppressing from the duplicate copy one or more data signals generated from the geometric aspects of the U-bend region; and generating the duplicate copy separate from the historic data set and the current data set representative of a change in condition of a tube of the number of tubes between the first time and the second time.

2. The method of claim 1, wherein the collecting at the first time the historic data set comprises collecting the historic data set prior to the time the steam generator is placed in service.

3. The method of claim 1, wherein the collecting at the first time, the historic data set comprises collecting the historic data set during an in-service inspection of the steam generator.

4. The method of claim 1, further comprising:

collecting at an additional time an additional historic data set for each of at least some of the number of tubes, the additional time being between the first time and the second time; and comparing the current data set with both the historic data set and the additional historic data set to generate the another data set.

5. The method of claim 1, further comprising:

collecting as the historic data set a set of amplitude and phase values for each of a plurality of data points in the U-bend region or other signal of interest for each of at least some of the number of tubes; and collecting as the current data set a set of amplitude and phase values for each of a plurality of data points in the tube sheet transition region or the other signal of interest for each of at least some of the number of tubes.

6. The method of claim 1, further comprising:

determining a difference in operating parameters between a first set of instrumentation that was employed in collecting the historic data set and a second set of instrumentation that was employed in collecting the current data set; and applying at least a portion of the difference in operating parameters to one of the historic data set and the current data set to scale the one of the historic data set and the current data set.

7. The method of claim 1, further comprising reversing at least a portion of one of the historic data set and the current data set to enable comparison of the historic and current data sets despite collection of the historic and current data sets in opposite longitudinal directions along the tube.

8. The method of claim 1, further comprising validating said another data set generated to confirm said suppressing from the merged data set aspects that were present in the historic data set was suitably performed, and to confirm acceptability of calibrated signal characteristics selected from the group consisting of signal amplitude, phase, pattern, signal width, and signal area.

* * * * *